United States Patent
Dix et al.

(10) Patent No.: US 11,806,398 B2
(45) Date of Patent: *Nov. 7, 2023

(54) CITRATE BUFFERED VEGF ANTAGONIST FORMULATIONS

(71) Applicant: REGENERON PHARMACEUTICALS, INC., Tarrytown, NY (US)

(72) Inventors: Daniel B. Dix, LaGrangeville, NY (US); Kelly Frye, Mendham, NJ (US); Susan Kautz, Albany, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 340 days.

This patent is subject to a terminal disclaimer.

(21) Appl. No.: 16/950,584

(22) Filed: Nov. 17, 2020

(65) Prior Publication Data

US 2021/0077624 A1    Mar. 18, 2021

Related U.S. Application Data

(60) Continuation of application No. 16/535,610, filed on Aug. 8, 2019, now Pat. No. 10,857,231, which is a continuation of application No. 15/692,893, filed on Aug. 31, 2017, now Pat. No. 10,406,226, which is a continuation of application No. 15/342,989, filed on Nov. 3, 2016, now abandoned, which is a continuation of application No. 15/064,343, filed on Mar. 8, 2016, now Pat. No. 9,511,140, which is a continuation of application No. 14/550,385, filed on Nov. 21, 2014, now Pat. No. 9,416,167, which is a continuation of application No. 13/909,745, filed on Jun. 4, 2013, now Pat. No. 8,921,316, which is a continuation of application No. 13/428,510, filed on Mar. 23, 2012, now Pat. No. 8,710,004, which is a continuation of application No. 13/343,214, filed on Jan. 4, 2012, now Pat. No. 8,404,638, which is a division of application No. 12/835,065, filed on Jul. 13, 2010, now Pat. No. 8,110,546, which is a continuation of application No. 11/387,256, filed on Mar. 22, 2006, now abandoned.

(60) Provisional application No. 60/665,125, filed on Mar. 25, 2005.

(51) Int. Cl.
| | |
|---|---|
| A61K 39/395 | (2006.01) |
| A61K 38/17 | (2006.01) |
| A61K 9/00 | (2006.01) |
| A61K 9/08 | (2006.01) |
| A61K 31/7012 | (2006.01) |
| A61K 47/02 | (2006.01) |
| A61K 47/26 | (2006.01) |
| A61K 38/16 | (2006.01) |
| A61K 47/10 | (2017.01) |
| C07K 14/71 | (2006.01) |
| C07K 16/22 | (2006.01) |
| A61K 47/12 | (2006.01) |
| A61K 9/19 | (2006.01) |
| A61K 31/4172 | (2006.01) |
| A61K 47/18 | (2017.01) |
| A61K 47/22 | (2006.01) |

(52) U.S. Cl.
CPC ...... *A61K 39/39591* (2013.01); *A61K 9/0019* (2013.01); *A61K 9/08* (2013.01); *A61K 9/19* (2013.01); *A61K 31/4172* (2013.01); *A61K 31/7012* (2013.01); *A61K 38/16* (2013.01); *A61K 38/179* (2013.01); *A61K 47/02* (2013.01); *A61K 47/10* (2013.01); *A61K 47/12* (2013.01); *A61K 47/183* (2013.01); *A61K 47/22* (2013.01); *A61K 47/26* (2013.01); *C07K 14/71* (2013.01); *C07K 16/22* (2013.01); *C07K 2318/20* (2013.01); *C07K 2319/30* (2013.01)

(58) Field of Classification Search
CPC ...... A61K 39/39591; A61K 9/19; A61K 9/08; C07K 16/22
See application file for complete search history.

(56) References Cited

U.S. PATENT DOCUMENTS

| | | | |
|---|---|---|---|
| 5,399,670 | A | 3/1995 | Bhattacharya et al. |
| 5,763,401 | A | 6/1998 | Nayar |
| 5,851,999 | A | 12/1998 | Ulrich et al. |
| 6,011,003 | A | 1/2000 | Charmock-jonee et al. |
| 6,100,071 | A | 8/2000 | Davis-Smyth et al. |
| 6,171,586 | B1 | 1/2001 | Lam et al. |
| 6,267,958 | B1 | 7/2001 | Andya et al. |
| 6,270,993 | B1 | 8/2001 | Shibuya et al. |
| 6,472,179 | B2 | 10/2002 | Stahl et al. |
| 6,676,941 | B2 | 1/2004 | Thorpe et al. |

(Continued)

FOREIGN PATENT DOCUMENTS

| | | |
|---|---|---|
| CA | 2569108 A1 | 12/2005 |
| CA | 2598711 | 10/2006 |

(Continued)

OTHER PUBLICATIONS 4.1.3. Buffer solutions, European Pharmacopoeia 5.0, 431-434 (2004).

(Continued)

*Primary Examiner* — Elly-Gerald Stoica
(74) *Attorney, Agent, or Firm* — Arnold & Porter Kaye Scholer LLP

(57) ABSTRACT

Formulations of a vascular endothelial growth factor (VEGF)-specific fusion protein antagonist are provided including a pre-lyophilized formulation, a reconstituted lyophilized formulation, and a stable liquid formulation. Preferably, the fusion protein has the sequence of SEQ ID NO:4.

28 Claims, No Drawings

Specification includes a Sequence Listing.

(56) References Cited

U.S. PATENT DOCUMENTS

| | | |
|---|---|---|
| 6,833,349 B2 | 12/2004 | Xia et al. |
| 6,875,432 B2 | 4/2005 | Liu et al. |
| 6,897,294 B2 | 5/2005 | Davis-Smyth et al. |
| 7,001,892 B1 | 2/2006 | Chmielweski et al. |
| 7,052,691 B2 | 5/2006 | Sleeman et al. |
| 7,060,268 B2 | 6/2006 | Andya et al. |
| 7,070,959 B1 | 7/2006 | Papadopoulos et al. |
| 7,087,411 B2 | 8/2006 | Daly et al. |
| 7,374,757 B2 | 5/2008 | Papadopoulos et al. |
| 7,374,758 B2 | 5/2008 | Papadopoulos et al. |
| 7,482,002 B2 | 1/2009 | Cedarbaum |
| 7,608,261 B2 | 10/2009 | Furfine et al. |
| 7,750,138 B2 | 7/2010 | Fang et al. |
| 7,807,164 B2 | 10/2010 | Furfine et al. |
| 7,951,585 B2 | 5/2011 | Ke |
| 8,084,234 B2 | 12/2011 | Papadopoulos et al. |
| 8,092,803 B2 | 1/2012 | Furfine et al. |
| 8,110,546 B2 | 2/2012 | Dix et al. |
| 8,216,575 B2 | 7/2012 | Yu |
| 8,343,737 B2 | 1/2013 | Papadopoulos et al. |
| 8,404,638 B2 | 3/2013 | Dix et al. |
| 8,481,046 B2 | 7/2013 | Furfine et al. |
| 8,647,842 B2 | 2/2014 | Papadopoulos et al. |
| 8,710,004 B2 | 4/2014 | Dix et al. |
| 8,802,107 B2 | 8/2014 | Furfine et al. |
| 8,921,316 B2 | 12/2014 | Dix et al. |
| 9,340,594 B2 | 5/2016 | Furfine et al. |
| 9,416,167 B2 | 8/2016 | Dix et al. |
| 9,511,140 B2 | 12/2016 | Dix et al. |
| 9,580,489 B2 | 2/2017 | Furfine et al. |
| 9,636,400 B2 | 5/2017 | Dix et al. |
| 9,657,084 B2 | 5/2017 | Ke et al. |
| 9,914,763 B2 | 3/2018 | Furfine et al. |
| 10,400,025 B2 | 9/2019 | Furfine et al. |
| 10,406,226 B2 | 9/2019 | Dix et al. |
| 10,464,992 B2 | 11/2019 | Furfine et al. |
| 10,857,231 B2 | 12/2020 | Dix et al. |
| 11,066,458 B2 | 7/2021 | Furfine et al. |
| 11,084,865 B2 | 8/2021 | Furfine et al. |
| 2001/0014326 A1 | 8/2001 | Andya et al. |
| 2002/0004478 A1 | 1/2002 | Danko et al. |
| 2003/0092606 A1 | 5/2003 | L'Italien et al. |
| 2003/0113316 A1 | 6/2003 | Kaisheva et al. |
| 2003/0138417 A1 | 7/2003 | Kaisheva et al. |
| 2003/0202972 A1 | 10/2003 | Andya et al. |
| 2004/0014667 A1 | 1/2004 | Daly et al. |
| 2004/0197324 A1 | 10/2004 | Liu et al. |
| 2004/0213787 A1 | 10/2004 | Sleeman et al. |
| 2004/0265309 A1 | 12/2004 | Kandel et al. |
| 2004/0266688 A1 | 12/2004 | Nayak |
| 2005/0004027 A1 | 1/2005 | Wiegand et al. |
| 2005/0032699 A1 | 2/2005 | Holash et al. |
| 2005/0043236 A1 | 2/2005 | Daly et al. |
| 2005/0112061 A1 | 5/2005 | Holash et al. |
| 2005/0276808 A1 | 12/2005 | Cedarbaum |
| 2005/0281822 A1 | 12/2005 | Cedarbaum et al. |
| 2005/0281831 A1 | 12/2005 | Davis-Smyth et al. |
| 2006/0030000 A1 | 2/2006 | Alitalo et al. |
| 2006/0058234 A1 | 3/2006 | Daly et al. |
| 2006/0217311 A1 | 9/2006 | Dix et al. |
| 2008/0085276 A1 | 4/2008 | Wiegand et al. |
| 2009/0264358 A1 | 10/2009 | Yu et al. |
| 2012/0101035 A1 | 4/2012 | Dix et al. |
| 2012/0178683 A1 | 7/2012 | Dix et al. |
| 2013/0261056 A1 | 10/2013 | Dix et al. |
| 2014/0012227 A1 | 1/2014 | Sigg et al. |
| 2015/0079087 A1 | 3/2015 | Dix et al. |
| 2016/0144025 A1 | 5/2016 | Vitti et al. |
| 2016/0175439 A1 | 6/2016 | Dix et al. |
| 2017/0073407 A1 | 3/2017 | Dix et al. |
| 2017/0360930 A1 | 12/2017 | Dix et al. |

FOREIGN PATENT DOCUMENTS

| | | |
|---|---|---|
| CN | 1304427 C | 3/2007 |
| CN | 100502945 C | 6/2009 |
| CN | 100567325 C | 12/2009 |
| CN | 102233132 B | 10/2013 |
| CN | 102380096 B | 4/2014 |
| CN | 103212075 B | 6/2017 |
| CN | 107115294 A | 9/2017 |
| EP | 2944306 | 1/2021 |
| JP | H10273450 | 10/1998 |
| JP | H11510170 | 9/1999 |
| JP | 2002516871 | 6/2002 |
| WO | WO1993000807 | 1/1993 |
| WO | WO 1997/004801 A1 | 2/1997 |
| WO | WO 1998/045331 A2 | 10/1998 |
| WO | WO 1999/013909 A1 | 3/1999 |
| WO | WO1999013909 | 3/1999 |
| WO | WO 1999/062536 A2 | 12/1999 |
| WO | WO1999062536 | 12/1999 |
| WO | WO 2000/063380 A1 | 10/2000 |
| WO | WO 00/75319 | 12/2000 |
| WO | WO 2000/075319 A1 | 12/2000 |
| WO | WO2000753191 | 12/2000 |
| WO | WO2002060489 | 8/2002 |
| WO | WO 2003/072060 A2 | 9/2003 |
| WO | WO 2004/087206 A2 | 10/2004 |
| WO | WO 2004/091658 | 10/2004 |
| WO | WO2004103159 | 12/2004 |
| WO | WO2004106378 | 12/2004 |
| WO | WO2005000895 | 1/2005 |
| WO | WO 2005011734 | 2/2005 |
| WO | WO2005020972 | 3/2005 |
| WO | WO2005072772 | 8/2005 |
| WO | WO 2005/102303 A2 | 11/2005 |
| WO | WO2006/015297 | 2/2006 |
| WO | WO2006047325 | 5/2006 |
| WO | WO2006088650 | 8/2006 |
| WO | WO 2006/104852 | 10/2006 |
| WO | WO 2006/138181 A2 | 12/2006 |
| WO | WO 2007/112675 | 10/2007 |
| WO | WO2007149334 | 12/2007 |

OTHER PUBLICATIONS

Amand et al., Controllability analysis of protein glycosylation in CHO cells, PLOS One, 9(2): e87943 (2014) (16 pgs).
AMEVIVE® Label (Issued Sep. 2005) (2 pgs.).
Annex 1 (D21), filed in Opposition to European Patent No. 2 944 306 B1, 1 pg. (2021).
Anonymous, "Lucentis in the treatment of neovascular (wet) age-related macular degeneration (AMD)," 1-54 (2007).
Application for Extension of Patent Term Under 35 U.S.C. § 156 filed Dec. 22, 2011, in U.S. Pat. No. 7,374,758 (198 pgs.).
Arakawa et al., "Protein-Solvent Interactions in Pharmaceutical Formulations," *Pharmaceuticals Research*, 8(3):285-291 (1991).
AVASTIN® label, as submitted to the USPTO on Jan. 7, 2021, in Inter Partes Review No. IPR2021-00402 (2017) (37 pgs.).
Avery et al., "Intravitreal Bevacizumab (Avastin) for Neovascular Age-Related Macular Degeneration," *American Academy of Ophthalmology*, 113(3):363-372.e5 (Feb. 2006).
Back et al., "Increased Thermal Stability of Proteins in the Presence of Sugars and Polyols," *Biochemistry*, 18(23):5191-5196 (1979).
Baffert et al., "Age-Related Changes in Vascular Endothelial Growth Factor Dependency and Angiopoietin-1-Induced Plasticity of Adult Blood Vessels," *Circulation Research*, 984-992 (2004).
Bogard, Jr. et al., "Practical Considerations in the Production, Purification, and Formulation of Monoclonal Antibodies for Immunoscintigraphy and Immunotherapy," *Seminars in Nuclear Medicine*, XIX(3):202-220 (1989).
Borys et al., "Culture pH affects expression rates and glycosylation of recombinant mouse placental lactogen proteins by Chinese hamster ovary (CHO) cells," *Biotechnology*, 11:720-724 (1993).
Byrn et al., "Biological properties of a CD4 immunoadhesin," *Nature*, 344:667-670 (1990).

(56) References Cited

OTHER PUBLICATIONS

Capon et al., "Designing CD4 immunoadhesins for AIDS therapy," *Nature*, 337:525-531 (1989).
CARBOWAX™ Polyethylene Glycol (PEG) 3350 (1 pg.).
Carpenter et al., "Rational design of stable lyophilized protein formulations: some practical advice," *Pharm. Res.* 14(8): 969-975 (1997).
Chou et al., "Effects of Tween 20® and Tween 80® on the Stability of Albutropin During Agitation," *Journal of Pharmaceutical Sciences*, 94(6):1368-1381 (2005).
Christensen, "Proteins as Buffers," *Annals New York Academy of Sciences*, 133(1):34-40 (1966).
Cleland et al., "Formulation and Delivery of Proteins and Peptides," *American Chemical Society*, pp. 1-19 (1994).
Controls in SCI experiments, RegenBase, retrieved Jan. 6, 2021, from <http://regenbase.org/control-groups.html>, as submitted to the USPTO on Jan. 7, 2021, in Inter Partes Review No. IPR2021-00402, 2 pgs.
Daugherty et al., "Formulation and delivery issues for monoclonal antibody therapeutics," *Adv. Drug Delivery Rev.*, 58:668-706 (2006).
Declaration of Dan Dix executed Jun. 8, 2009, for U.S. Appl. No. 11/387,256 (3 pgs.).
Declaration of Daniel Dix, Ph.D. filed May 5, 2015, in European Patent Application No. 13152402.7 (4 pgs.).
Declaration of Dr. Ralph Tarantino in Support of Petition for Post Grant Review of U.S. Pat. No. 10,857,231, executed Sep. 7, 2021 (236 pgs.).
Declaration of Rachel J. Watters, submitted in Petition for Post Grant Review of U.S. Pat. No. 10,857,231, executed Sep. 3, 2021 (21 pgs.).
Declaration Pursuant to 37 C.F.R. § 1.131 of Daniel B. Dix, Kelly Frye, and Susan Kautz filed Nov. 22, 2011, in U.S. Appl. No. 12/835,065 (11 pgs.).
Diehl et al., "A Good Practice Guide to the Administration of Substances and Removal of Blood, Including Routes and Volumes," *Journal of Applied Toxicology*, 21:15-23 (2001).
Drug Vehicle (Code C927), National Cancer Institute (NCI), retrieved Jan. 6, 2021, from <https://ncithesaurus.nci.nih.gov/ncitbrowser/ConceptReport jsp?dictionary=NCI_Thesaurus&ns=ncit&code=C927 >, as submitted to the USPTO on Jan. 7, 2021, in Inter Partes Review No. IPR2021-00402, 1 pg.
Drug Approval Package: Avastin (Bevacizum) NDA #125085, 2 pgs. (2005).
Drug Approval Package: Lucentis (Ranibizumab) Injection Company: Genetech, Inc. Application No. 12156, 2 pgs (2006).
Drug Approval Package: Macugen (Pegaptanib Sodium) Injection Company: Eyetech Pharmaceuticals, Inc. Application No. 021756, , 2 pgs. (2005).
ENBREL® Label (Revised Jul. 2005) (64 pgs.).
Excerpts from Antibody Fusion Proteins (S.M. Chamow & A. Ashkenazi (eds.) 221-309 (1999).
EYLEA® Product Insert (Revised Mar. 2021) (32 pgs.).
EYLEA® Product Insert (Revised Jul. 2021) (36 pgs.).
Fast et al., "Physical Instability of a Therapeutic Fc Fusion Protein: Domain Contributions to Conformational and Colloidal Stability," *Biochemistry*, 48(49):11724-11736 (2009).
File History of U.S. Appl. No. 16/535,610, filed Aug. 8, 2019, which issued as U.S. Pat. No. 10,857,231 on Dec. 8, 2020 (283 pgs.).
Fransson et al., "Local Tolerance of Subcutaneous Injections," *J. Pharm. Pharmacol.*, 48:1012-1015 (1996).
Fraser et al., "Single Injections of Vascular Endothelial Growth Factor Trap Block Ovulation in the Macaque and Produced Prolonged, Dose-Related Suppression of Ovarian Function," *J. Clin. Endocrin. & Metabol.* 90(2):1114-1122 (2004).
Frenken et al., "Identification of the Component Part in an Epoetin Alfa Preparation That Causes Pain After Subcutaneous Injection," *American Journal of Kidney Diseases*, 22(4):553-556 (1993).
Frokjaer et al., "Pharmaceutical Formulation Development of Peptides and Proteins," Taylor & Francis, Philadelphia, PA, pp. 146-171 (2000).
Gasteiger et al., "ExPASy: the proteomics server for in-depth protein knowledge and analysis," *Nucleic Acids Research*, 31(13):3784-3788 (2003).
Glade-Blender et al., "VEFG Blocking Therapy in the Treatment of Cancer," *Expert Opinion on Biological Therapy*. Ashley London GB 3(2): 263-276 (Apr. 2003).
Gokarn et al., "Excipients for Protein Drugs," *Excipient Development for Pharmaceutical, Biotechnology, and Drug Delivery Systems*, 291-331 (2006).
Guidance for Industry Q1A(R2) Stability Testing of New Drug Substances and Products, U.S. Department of Health and Human Services, Food and Drug Administration, Rockville, MD, as submitted to the USPTO on Jan. 7, 2021, in Inter Partes Review No. IPR2021-00402, 25 pgs.
Harris, "Processing of C-terminal lysine and arginine residues of proteins isolated from mammalian cell culture," *Journal of Chromatography A*, 705:129-134 (1995).
HERCEPTIN® label (Sep. 1998) (2 pgs.).
Hermosilla et al., "Comprehensive biophysical and functional study of ziv-aflibercept: characterization and forced degradation," *Scientific Reports*, 10(2675):1-13 (2020).
Hirvonen et al., "Hydrodynamic Radii of Ranibizumab, Aflibercept and Bevacizumab Measured by Time-Resolved Phosphorescence Anisotropy," *Pharm Res*, 33:2025-2032 (2016).
Holash et al., "VEGF-Trap: A VEGF blocker with potent antitumor effects," *PNAS*, 99(17):11393-11398 (2002).
Hossler et al., "Optimal and consistent protein glycosylation in mammalian cell culture," *Glycobiology*, 19(9):936-949 (2009).
Huang et al., "Regression of established tumors and metastases by potent vascular endothelial growth factor blockade," *PNAS*, 100(13):7785-7790 (2003).
ICH, Guidance for Industry: Q5C Quality of Biotechnological Products: Stability Testing of Biotechnological/Biological Products, 9 pgs. (Jul. 1996).
Ich, Guidance for Industry: Q6B Specifications: Test Procedures and Acceptance Criteria for Biotechnological/Biological Products, 17 pgs. (Sep. 1999).
Intraocular Product Information, Physician's Desk Reference for Ophthalmology, pp. 318-319 (1999).
Intravitreal VEGF Trap looking promising, p. 1 (Feb. 21, 2006) <https://europe.ophthalmologytimes.com/view/intravitreal-vegf-trap-looking-promising>.
Jaissle et al., "Intravitreal injections—High Standards of Procedure Necessary," *Klin Monatsbl Augenheilkd*, 222:389, 4 pgs. (2005) (with English language translation).
Jefferis, "Glycosylation of Recombinant Antibody Therapeutics," *Biotechnol. Prog.*, 21:11-16 (2005).
Katayama et al., "Retrospective statistical analysis of lyophilized protein formulations of progenipoietin using PLS: determination of the critical parameters for long-term storage stability," *J. Pharm. Sci.*, 93(10): 2609-2623 (2004).
KEGG (Kyoto Encyclopedia of Genes and Genomes) Product Information Sheet for Aflibercept (1 pg.).
Kendrick et al., "Physical Stability of Proteins in Aqueous Solution," in *Rational Design of Stable Protein Formulations*, pp. 61-84, Kluwer Academic/Plenum publishers, New York, NY(2002).
Kerwin, "Polysorbates 20 and 80 Used in the Formulation of Protein Biotherapeutics: Structure and Degradation Pathways," *Journal of Pharmaceutical Sciences*, 97(8):2924-2935 (2008).
Kim et al., "Potent VEGF blockade causes regression of coopted vessels in a model of neuroblastoma," *PNAS*, 99(17):11399-11404 (2002).
Laursen et al., "Pain Perception after Subcutaneous Injections of Media Containing Different Buffers," *Basic & Clinical Pharmacology & Toxicology*, 98:218-221 (Jan. 2006).
LUCENTIS® label (2006) (2 pgs.).
LUCENTIS® label (2014) (14 pgs.).
Macugen® Label, NDA 21-756, pp. 4-11 (revised Jul. 2011).
Mi et al., "Effects of polyethylene glycol molecular weight and concentration on lactate dehydrogenase activity in solution and after freeze-thawing," *PDA J. Pharm. Sci. Technol.*, 56:115-123 (2002).
Moroney et al., "Aflibercept in epithelial ovarian carcinoma," *Future Oncol.*, 5(5):591-600 (2009).

(56) References Cited

OTHER PUBLICATIONS

Ng et al., "Pegaptanib, a targeted anti-VEGF aptamer for ocular vascular disease," *Nature Reviews*, 5:123-132 (Feb. 2006).
Ng et al., "Targeting angiogenesis, the underlying disorder in neovascular age-related macular degeneration," *Can J Ophthalmol*, 4(3):352-368 (2005).
Nguyen et al., "Results of a Phase I, Dose-Escalation, Safety, Tolerability, and Bioactivity Study of Intravitreous VEGF Trap in Patients With Neovascular Age-Related Macular Degeneration," *ARVO Annual Meeting Abstract*, pp. 1-2 (May 2006).
Non-Final Office Action dated Jul. 13, 2011, in U.S. Appl. No. 12/835,065 (8 pgs.).
Notice of Allowance dated Dec. 19, 2011, in U.S. Appl. No. 12/835,065 (12 pgs.).
Opposition to Patent Owner's Petition to Vacate Ex Parte Reexamination Order or, in the Alternative, to Stay Reexamination Proceeding Pursuant To 37 C.F.R. §§ 1.181 and 1.182 in Reexam Control No. 90/014,449, executed May 26, 2020 (31 pgs.).
Order Granting Request for Ex Parte Reexamination mailed Mar. 13, 2020, in Reexam Control No. 90/014,449 (13 pgs.).
ORENCIA® Label (Mar. 2017) (30 pgs.).
Patent Owner's Mandatory Notices (Case PGR2021-TBA) in U.S. Pat. No. 10,857,231, executed Sep. 24, 2021 (5 pgs.).
Petition for Post-Grant Review of U.S. Pat. No. 10,857,231 Under 35 U.S.C. §§ 321-329 and 37 C.F.R. § 42.200 ET SEQ. (Case PGR2021-TBA), executed Sep. 7, 2021 (103 pgs.).
Petition to Vacate Ex Parte Reexamination Order or, in the Alternative, to Stay Reexamination Proceeding Pursuant to 37 C.F.R. §§ 1.181 and 1.182 in Reexam Control No. 90/014,449, executed May 12, 2020 (30 pgs.).
Preliminary Response of Patent Owner Regeneron Pharmaceuticals, Inc. filed Apr. 14, 2021, in Case IPR2021-00402 (U.S. Pat. No. 10,464,992) (63 pgs.).
Phosphate buffer, Cold Spring Harbor Protocols, 2006:pdb.rec8543, as submitted to the USPTO on Jan. 7, 2021, in Inter Partes Review No. IPR2021-00402 (1 pg.).
RAPTIVA® label (Mar. 2009) (36 pgs.).
Redline Comparison of U.S. Pat. No. 10,857,231 B2, Issued Dec. 8, 2020 (Dix et at.) to U.S. Appl. No. 60/665,125 (14 pgs.).
Randolph et al., "Surfactant-Protein Interactions," *Rational Design of Stable Protein Formulations*, pp. 159-175, Springer, Boston, MA (2002).
REMICADE® label (2013) (58 pgs.).
Remington's Pharmaceutical Sciences, 18$^{th}$ Edition—Polysorbates (1990) (4 pgs.).
Request for Ex Parte Reexamination of U.S. Pat. No. 10,406,226 (Dix et al.), filed Feb. 11, 2020 (90 pgs.).
Response to Office Action Under 37 C.F.R. § 1.111 filed Dec. 6, 2016, in U.S. Appl. No. 15/150,840 (21 pgs.).
Response to Office Action Under 37 C.F.R. § 1.111 filed Nov. 22, 2011, in U.S. Appl. No. 12/835,065 (4 pgs.).
Ribeiro et al., "An Algorithm for the Computer Calculation of the Coefficients of a Polynomial that Allows Determination of Isoelectric Points of Proteins and Other Macromolecules," *Comput. Biol. Med.*, 20(4):235-242 (1990).
Rich et al., "Short-Term Safety and Efficacy of Intravitreal Bevacizumab (Avastin) for Neovascular Age-Related Macular Degeneration," *Retina, The Journal of Retinal and Vitreous Diseases*, 26(5):495-511 (May 2006).
Riss et al., "Choosing The Right Cell-Based Assay For Your Research," *Cell Notes*, 6:6-12 (2003).
Riss et al., "Use of Multiple Assay Endpoints to Investigate the Effects of Incubation Time, Dose of Toxin, and Plating Density in Cell-Based Cytotoxicity Assays," *ASSAY and Drug Development Technologies*, 2(1):51-75 (2004).
Riss, "Selecting Cell-Based Assays for Drug Discovery Screening," *Cell Notes*, 13:16-21 (2005).
Rosenfeld, "An Update on Bevacizumab," *Review of Ophthalmology*, 1-5 (Jan. 2006).

Saishin et al., "VEGF-TRAP$_{R1R2}$ Suppresses Choroidal Neovascularization and VEGF-Induced Breakdown of the Blood-Retinal Barrier," *Journal of Cellular Physiology*, 195:241-248 (2003).
Securities Daily, Announcement of Chengdu Kanghong Pharmaceutical Group Co., Ltd. on stopping the global multi-center clinical trial of Conbercept ophthalmic injection (Apr. 13, 2021) (with English language machine translation), available at <http://epaper.zqrb.cn/html/2021-04/10/content_716426.htm?div=-1.>.
Shukla et al., "Downstream Processing of Fc-Fusion Proteins," *Therapeutic Fc-Fusion Proteins*, 97-114 (2014).
Shukla et al., "Protein aggregation kinetics during Protein A chromatography Case study for an Fc fusion protein," *Journal of Chromatography A*, 1171:22-28 (2007).
SIMULECT® label, as submitted to the USPTO on Jan. 7, 2021, in Inter Partes Review No. IPR2021-00402 (1998) (7 pgs.).
Souillac, "Biophysical Characterization of Insoluble Aggregates of a Multi-Domain Protein: An Insight into the Role of the Various Domains," Journal of Pharmaceutical Sciences, 94:2069-2083 (2005).
Stewart, "Clinical and differential utility of VEGF inhibitors in wet age-related macular degeneration: focus on aflibercept," *Clinical Ophthalmology*, 6; 175-1186 (2012).
Strickley, "Solubilizing Excipients in Oral and Injectable Formulations," *Pharmaceutical Research*, 21(2):201-230 (2004).
Tang, China's Kanghong Pharma Hits Limit Down as France Stops Trials of Ophthalmic Drug, YiCai Global (Mar. 29, 2021) https://www.yicaiglobal.com/news/china-kanghong-pharma-hits-limit-down-as-france-stops-trials-of-ophthalmic-drug.
Thorpe et al., "The Use of Bioassays for the Characterisation and Control of Biological Therapeutic Products Produced by Biotechnology," *Dev. Biol. Stand*, 91:79-88 (1997).
Van Slyke, "On the Measurement of Buffer Values and on the Relationship of Buffer Value to the Dissociation Constant of the Buffer and the Concentration and Reaction of the Buffer Solution," *Hospital of The Rockefeller Institute for Medical Research*, 525-570 (1922).
Voight, "Injection and infusion preparations," *Pharmazeutische Technologie*, 461-462 (2006) (with English language translation).
Wang, "Instability, stabilization, and formulation of liquid protein pharmaceuticals," *International Journal of Pharmaceutics*, 185:129-188 (1999).
Wang et al., "Antibody Structure, Instability, and Formulation," *Journal of Pharmaceutical Sciences*, 96(1)1-26 (2007).
Wang, "Protein aggregation and its inhibition in biopharmaceutics," *International Journal of Pharmaceutics*, 289:1-30 (2005).
Wang et al., "Glycoengineering of CHO cells to improve product quality," Paula Meleady (ed.), Heterologous Protein Production in CHO Cells: Methods and Protocols, Methods in Molecular Biology, vol. 1603: 25-44, DOI 10.1007/978-1-4939-6972-2_2, © Springer Science+Buisness Media LLC (2017).
Webb et al., "A new mechanism for decreasing aggregation of recombinant human interferon-gamma by a surfactant: slowed dissolution of lyophilized formulations in a solution containing 0.03% polysorbate 20," *J. Pharm. Sci*, 93(10): 2609-2623(2002).
White et al., "Best practices in bioassay development to support registration of biopharmaceuticals," *BioTechniques*, 67(3):126-137 (2019).
Winter et al., "Man-made antibodies," *Nature*, 349:293-299 (1991).
XOLAIR® label (2003) (17 pgs.).
Amersham Biosciences, Antibody Purification Handbook, 18-1037-46, pp. 5-107 (2002).
Andersen et al., "Recombinant protein expression for therapeutic applications," Current Opinion in Biotechnology, 13:117-123 (2002).
Bontempo, "Preformulation Development of Parenteral Biopharmaceuticals," Drugs and the Pharmaceutical Sciences, 85:91-108 (1997).
Chi et al., "Physical Stability of Proteins in Aqueous Solution: Mechanism and Driving Forces in Nonnative Protein Aggregation," Pharmaceutical Research, 20(9):1325-1336 (2003).
Janeway et al., "The structure of a typical antibody molecule," Immunobiology: The Immune System in Health and Disease, 5th edition, New York: Garland Science, 6 pgs. (2001).
Parkins et al., "The formulation of biopharmaceutical products," Pharmaceutical Science & Technology Today, 3(4):129-137 (2000).

(56) References Cited

OTHER PUBLICATIONS

Routier et al., "The glycosylation pattern of a humanized IgG1 antibody (D1.3) expressed in CHO cells," Glycoconjugate J., 14:201-207 (1997).
Rudd et al., "Glycosylation: Heterogeneity and the 3D Structure of Proteins," Critical Reviews in Biochemistry & Molecular Bio., 32(1):1-100 (1997).
Rudge et al., "VEGF Trap as a Novel Antiangiogenic Treatment Currently in Clinical Trials for Cancer and Eye Diseases, and VelociGene®-based Discovery of the Next Generation of Angiogenesis Targets," Cold Spring Harbor Symposia on Quantitative Biology, 70:411-418 (2004).
Wulff et al., "Prevention of Thecal Angiogenesis, Antral Follicular Growth, and Ovulation in the Primate by Treatment with Vascular Endothelial Growth Factor Trap R1R2,"Endocrinology, 143(7):2797-2807 (2002).
Amand et al., Controllability analysis of protein glycosylation in CHO cells, PLOS One, 9, e87943, 2014. (Year: 2014).
Borys et al., Culture pH affects expression rates and glycosylation of recombinant mouse placental lactogen proteins by Chinese hamster ovary (CHO) cells, Biotechnology, 11, 720-724, 1993. (year: 1993).
Carpenter, J.F. (1997) Rational Design of Stable Lyophilized . . . , Pharm. Res. 14(8): 969-975.
Daugherty et al., (2006) Formulation and delivery issues for monoclonal . . . , Adv. Drug Delivery Rev. 58:668-706.
Fraser et al. (2004) Single injection of Vascular Trap . . . , J. Clin. Endocrin. & Metabol. 90(2): 1114-1122.
Glade-Blender, J. et al., VEFG Blocking Therapy in the Treatment of Cancer, Expert Opinion on Biological Therapy. Ashley London GB vol. 3, No. 2 Apr. 2003, pp. 263-276.
Hanks Solution http://www.lifetechnologies.com/us/en/home/technical-resources/media-formulation.152.html.
Holash, Jocelyn et al., (2002) VEGF-Trap: AVEGF blocker with potent antitumor effects, Proceedings of the National Academy of Sciences of the United States of America, vol. 99 No. 17 Aug. 20, 2002, 11393-11398.
Katayama, et al., (2004) Retrospective statistical analysis of lyophilized . . . , J. Phrm. Sci. 93(10): 2609-2623.
Kendrick et al., Physical Stability of Proteins in Aqueous Solution in Rational Design of Stable Protein Formulations pp. 61-84 (relabeled as pp. 1-19 in provided version), published 2002, Kluwer Academic/Plenum publishers, New York, NY.
Kim, Eugene S. et al., Proceedings of the National Academy of Sciences of the United States of America, vol. 99, No, 17, Aug. 20, 2002.
Lopez et al., "Comparative enhancer effects of Span 20 with Tween 20 and Azone of the in vitro percutaneous penetration of compounds with different lipophilicites" International Journal of Pharmaceutics (Jul. 1, 2000) 202(1-2):133-140.
Mi et al., (2002) Effects of polyethylene glycol molecular weight and concentration . . . , PDS J. Pharm. Sci. Technol., 56;115-123.
Randolph and Jones, "Surfactant-Protein Interactions in Rational Design of Stable Protein Formulations," pp. 159-175, published 2002, Kluwer Academic/Plenum publishers, New York, NY.
Stewart, M.W. (2012) Clinical and Differential utility of VEGF Inhibitors . . . , Clinical Ophthalmology, 2012:6; 175-1186.
Wang et al., Glycoengineering of CHO cells to improve product quality. Paula Meleady (ed.), Heterologous Protein Production in CHOCells: Methods and Protocols, Methods in Molecular Biology, vol. 1603, DOI 10.1007/978-1-4939-6972-2_2, © Springer Science+Buisness Media LLC 2017. (Year: 2017).
Wang, W. (1999) Instability, stabilization and formulation of liquid protein . . . , Int'l J. Pharmaceutics 185(2): 129-188.
Webb et al. (2002) A new mechanism for decreasing aggregation . . . , J. Pharm. Sci 93(10): 2609-2623.
Declaration in Support of Request for Ex Parte Reexamination of U.S. Pat. No. 10,406,226 (Dix et al.) by Steven M. Chamow, Ph.D. executed Feb. 5, 2020.
File History of U.S. Appl. No. 15/692,893, filed Aug. 31, 2017, which issued as U.S. Pat. No. 10/406,226 on Sep. 10, 2019.
U.S. Appl. No. 11/387,256, filed Mar. 22, 2006 (application as filed).
U.S. Appl. No. 60/665,125, filed Mar. 25, 2005 (application as filed).
Terminal Disclaimer for U.S. Appl. No. 15/151,776, filed Oct. 18, 2016.
Terminal Disclaimer for U.S. Appl. No. 15/095,606, filed Oct. 5, 2017.
U.S. Appl. No. 17/307,240, filed May 4, 2021, which is pending.
U.S. Appl. No. 17/314,992, filed May 7, 2021, which is pending.
U.S. Appl. No. 17/308,801, filed May 5, 2021, which is pending.
U.S. Appl. No. 17/313,627, filed May 6, 2021, which is pending.
U.S. Appl. No. 16/535,610, filed Aug. 8, 2019, which issued as U.S. Pat. No. 10,857,231 on Dec. 8, 2020. A statutory disclaimer was filed in the '231 Patent on Mar. 14, 2022, which was published in the Official Gazette on Mar. 14, 2023.
U.S. Appl. No. 15/692,893 filed Aug. 31, 2017, which issued as U.S. Pat. No. 10,406,226 on Sep. 10, 2019.
U.S. Appl. No. 15/342,989, filed Nov. 3, 2016, which is abandoned.
U.S. Appl. No. No. 15/150,840, filed May 10, 2016, which issued as U.S. Pat. No. 9,636,400 on May 2, 2017.
U.S. Appl. No. 15/064,343, filed Mar. 8, 2016, which issued as U.S. Pat. No. 9,511,140 on Dec. 6, 2016.
U.S. Appl. No. 14/550,385, filed Nov. 21, 2014, which issued as U.S. Pat. No. 9,416,167 on Aug. 16, 2016.
U.S. Appl. No. 13/909,745, filed Jun. 4, 2013, which issued as U.S. Pat. No. 8,921,316 on Dec. 30, 2014.
U.S. Appl. No. No. 13/428,510, filed Mar. 23, 2012, which issued as U.S. Pat. No. 8,710,004 on Apr. 29, 2014.
U.S. Appl. No. 13/343,214, filed Jan. 4, 2012, which issued as U.S. Pat. No. 8,404,638 on Mar. 26, 2013.
U.S. Appl. No. 12/835,065, filed Jul. 13, 2010, which issued as U.S. Pat. No. 8,110,546 on Feb. 7, 2012.
U.S. Appl. No. 11/387,256, filed Mar. 22, 2006, which is abandoned.
Ex parte Reexamination No. 90/014,449 of U.S. Pat. No. 10,406,226 filed on Feb. 11, 2020.
Inter Parles Review Application No. IPR2023-00620 of U.S. Pat. No. 10,406,226, filed on Feb. 28, 2023.
Post-Grant Review No. PGR2021-00117 of U.S. Pat. No. 10,857,231, filed on Sep. 7, 2021. A Decision Denying Institution of Inter Partes Review was issued on Mar. 15, 2022.
Amin et al., "Lyophilization of Polyethylene Glycol Mixtures," *Journal of Pharmaceutical Sciences*, 93(9): pp. 2244-2249 (2004).
Andya et al., "Mechanisms of Aggregate Formation and Carbohydrate Excipient Stabilization of Lyophilized Humanized Monoclonal Antibody Formulations," *AAPS PharmSci*, 5(2): Article 10, pp. 1-11 (Apr. 2003).
ARANESP® Prescribing Information (Revised Jun. 2011) (41 pgs.).
Atkinson et al., "Formulation Strategies for Biopharmaceuticals Enduring Success to Market," *The Investigational Drugs Journal*, 4(5): pp. 557-560 (2001).
Avastin® (Bevacizumab) label, Center for Drug Evaluation and Research Approval Package for: Application No. STN-125085/0, pp. 1-28 (2004).
Avastin® (Bevacizum) Drug Approval Package, NDA #12508, https://www.accessdata.fda.gov/drugsatfda_docs/nda/2004/STN-125085_Avastin.cfm, 2 pp. (created Mar. 8, 2005).
Certificate of Correction dated Mar. 3, 2020, in U.S. Pat. No. 10,464,992, 1 Pg.
Chang et al., "Practical Approaches to Protein Formulation Development," in *Rational Design of Stable Protein Formulations—Theory and Practice* (J.F. Carpenter and M.C. Manning eds.), Kluwer Academic/Plenum pubs. (NY), pp. 1-25 (2002).
Cleland et al, "The Development of Stable Protein Formulations: A Close Look at Protein Aggregation, Deamidation, and Oxidation," *Critical Reviews in Therapeutic Drug Carrier Systems*, 10(4): pp. 307-377 (1993).
Decision on Petition Under 37 CFR 1.181 mailed Sep. 30, 2021, in Reexam Control No. 90/014,448 (10 pgs.).

(56) References Cited

OTHER PUBLICATIONS

Declaration of Dr. Reiner Gentz, as submitted to the USPTO on Jan. 7, 2021, in Inter Partes Review No. IPR2021-00402, 76 pgs.
Declaration of Prof Clive Wilson, filed in Opposition to European Patent No. 2 944 306 B1, executed Oct. 26, 2021 (75 pgs.).
*Development and Manufacture of Protein Pharmaceuticals*, Steven L. Nail and Michael J. Akers (eds.), Pharmaceutical Biotechnology, vol. 14, DOI 10.1007/978-1-4615-0549-5, © Springer Science+Business Media New York (2002).
Disclaimer In Patent Under 37 C.F.R. § 1.321(a) of Frank R. Cottingham, Ph.D., J.D., in U.S. Pat. No. 10,857,231, executed Mar. 14, 2022 (1 pg.).
Dunleavy, "Special Reports: Humira," Fiercepharma (May 3, 2021) <https://www.fiercepharma.com/special-report/top-20-drugs-by2020-sales-humira> (Accessed on Nov. 19, 2021).
EPOGEN® Prescribing Information (Revised Sep. 2017) (59 pgs.).
European Search Report dated Aug. 4, 2011, in EP Application 11157965.
European Search Report dated Aug. 12, 2015, in EP Application 15169936.
European Search Report dated Nov. 12, 2020, in EP Application 20178021.
European Search Report dated Feb. 28, 2013, in EP Application 13152402.
Ex Parte Request for Reexamination of U.S. Pat. No. 10,464,992, pp. 1-70, published Feb. 11, 2020.
Expert Declaration of Dr. Peter Tessier in Support of Petition for Inter Partes Review of U.S. Pat. No. 10,406,226, dated Feb. 23, 2023, in IPR2023-00620 (60 pgs.).
Expert Declaration of Dr. Ralph Tarantino in Support of Petition for Inter Partes Review of U.S. Pat. No. 10,464,992, filed Jan. 17, 2023, in IPR2023-00462 (85 pgs.).
EYLEA® Product Insert (Revised Feb. 2023) (40 pp.).
Fahrner et al., "Industrial Purification of Pharmaceutical Antibodies: Development, Operation, and Validation of Chromatography Processes," *Biotechnology and Genetic Engineering Reviews*, 18(1):pp. 301-327 (Jul. 2001).
Ferrara et al., "Angiogenesis as a therapeutic target," *Nature*, 438: pp. 967-974 (Dec. 2005).
File History of U.S. Pat. No. 10,464,992, as submitted to the USPTO on Jan. 7, 2021, in Inter Partes Review No. IPR2021-00402, 124 pgs.
GONAL-F® Prescribing Information (Revised Dec. 2020) (33 pgs.).
HERCEPTIN®, *Physician's Desk Reference*, 59th Ed., Thompson PDR (NJ), pp. 313 & 1337-1341 (2005).
HUMALOG® Prescribing Information (Mar. 2013) (27 pgs.).
HUMIRA™ Label (Dec. 20, 2002) (17 pgs.).
INFERGEN® Prescribing Information (Revised Jul. 2010) (39 pgs.).
International Preliminary Report on Patentability dated Sep. 25, 2007, for International Application PCT/US2006/010600.
International Search Report dated Sep. 19, 2006, for International Appln. PCT/US2006/010600.
International Search Report dated Apr. 3, 2008, in International Appln. PCT/US2007/014085.
INTRON® A Prescribing Information (Revised Nov. 1997) (37 pgs.).
Ionescu et al., "Contribution of Variable Domains to the Stability of Humanized IgG1 Monoclonal Antibodies," *J. Pharm. Sci.*, 97(4):1414-1426 (Apr. 2008).
IPR2023-00462, Paper 2, Petition for Inter Partes Review of U.S. Pat. No. 10,464,992 (77 pgs.) (Jan. 17, 2023).
IPR2023-00620, Paper 2, Petition for Inter Partes Review of U.S. Pat. No. 10,406,226 (75 pgs.).
Kalantar-Zadeh, "History of Erythropoiesis-Stimulating Agents, the Development of Biosimilars, and the Future of Anemia Treatment in Nephrology,"*American Journal of Nephrology*, 45: pp. 235-247 (2017).

KINERET® Prescribing Information (Revised Dec. 2020) (18 pgs.).
Kostanski et al., "Size-exclusion chromatography—a review of calibration methodologies,"*J. Biochem. Biophys. Methods*, 58: pp. 159-186 (2004).
Krapp et al., "Structural Analysis of Human IgG-Fc Glycoforms Reveals a Correlation Between Glycosylation and Structural Integrity,"*Journal of Molecular Biology*, 325(5):pp. 979-989 (2003).
Krishnan et al., "Development of Formulations for Therapeutic Monoclonal Antibodies and Fc Fusion Proteins,"in *Formulation and Process Development Strategies for Manufacturing Biopharmaceuticals*, pp. 383-427, John Wiley & Sons, Inc., New Jersey, NY (2010).
Liu, "Antibody Glycosylation and Its Impact on the Pharmacokinetics and Pharmacodynarnics of Monoclonal Antibodies and Fc-Fusion Proteins,"*Journal of Pharmaceutical Sciences*, 104:pp. 1866-1884 (Apr. 14, 2015).
Macugen® (Pegaptanib Sodium) Injection Drug Approval Package, FDA database, NDA #021756, 2 pp. (created Mar. 23, 2005).
Malingre et al., "The Co-Solvent Cremophor EL Limits Absorption of Orally Administered Paclitaxel in Cancer Patients," *British Journal of Cancer*, 85(10): pp. 1472-1477 (2001).
McGoff et al., "Solution Formulation of Proteins/Peptides,"in *Drugs and the Pharmaceutical Sciences, vol. 99: Protein Formulation and Delivery* (E.J. McNally ed.), Marcel Dekker, Inc. pub. (NY), pp. 139-158 (2000).
Mimura et al., "The role of oligosaccharide residues of IgG1-Fc in FcγIIb binding,"*Journal of Biological Chemistry*, 276(49):45539-45547 (Sep. 20, 2001).
Molecular Approaches to Controlling Cancer, Cold Spring Harbor Symposia on Quantitative Biology, vol. LXX, pp. xxvii-xxix (2005).
NOVOLOG® Prescribing Information (Revised Feb. 2015) (51 pgs.).
NUTROPIN AQ® Prescribing Information (Revised Dec. 2016) (23 pgs.).
Opposition to Patent Owner's Petition to Vacate Ex Parte Reexamination Order or, in the Alternative, to Stay Reexamination Proceeding Pursuant To 37 C.F.R. §§ 1.181 and 1.182 in Reexam Control No. 90/014,448, executed Jun. 12, 2020 (53 pgs.).
Order Denying Institution of Post-Grant Review Pursuant to 35 U.S.C. § 324, entered Mar. 15, 2022, in Case PGR2021-00117 (U.S. Pat. No. 10,857,231) (4 pgs.).
Order Granting Request for Ex Parte Reexamination mailed Apr. 1, 2020, in Reexam Control No. 90/014,448 (21 pgs.).
Order Granting Unopposed Motions to Dismiss the Petition and Terminate the Proceeding Before Institution 37 C.F.R. §§ 42.5(a), 42.71(a) entered Jun. 25, 2021, in Inter Partes Review No. IPR2021-00402 (U.S. Pat. No. 10,464,992 B2)/PGR2021-00035 (U.S. Pat. 10,828,345 B2) (3 pgs.).
Park, Press Release, "Nucala 40mg Prefilled Syringe Approved for Children with Severe Eosinophilic Asthma,"(Jan. 25, 2022).
Patent Owner Regeneron Pharmaceuticals, Inc.'s Sur-Reply to Petitioner's Reply to Patent Owner Preliminary Response, filed Jan. 25, 2022, in Case PGR2021-00117 (U.S. Pat. No. 10,857,231) (14 pgs.) (later withdrawn by the PTAB).
Patent Owner Regeneron Pharmaceuticals, Inc.'s Unopposed Motion to Withdraw Patent Owner's Preliminary Response and Surreply, filed Mar. 3, 2022, in Case PGR2021-00117 (U.S. Pat. No. 10,857,231) (4 pgs.).
Patent Owner's Mandatory Notices dated Jan. 25, 2021, in Inter Partes Review No. IPR2021-00402 (7 pgs.).
Patro et al., "Protein Formulation and Fill-Finish Operations," *Biotechnology Annual Review*, 8:55-84 (2002).
Petition for Inter Partes Review of U.S. Pat. No. 10,464,992 Under 35 U.S.C. §§ 311-319 and 37 C.F.R. § 42.100 et seq. (Inter Partes Review No. IPR2021-00402), executed Jan. 7, 2021 (59 pgs.).
Petition to Vacate Ex Parte Reexamination Order or, in the Alternative, to Stay Reexamination Proceeding Pursuant to 37 C.F.R. §§ 1.181 and 1.182 in Reexam Control No. 90/014,448, executed May 29, 2020 (33 pgs.).
Petitioner's Unopposed Motion to Terminate Proceedings Pursuant to 35 U.S.C. § 317(A) dated Jun. 23, 2021, in Inter Partes Review No. IPR2021-00402 (5 pgs.).

(56) References Cited

OTHER PUBLICATIONS

Petitioner's Reply to Patent Owner's Preliminary Response, filed Jan. 18, 2022, in Case PGR2021-00117 (U.S. Pat. No. 10,857,231) (16 pgs.).
Pre-filled Syringe, Collins Dictionary, https://www.collinsdictionary.com/de/worterbuch/englisch/pre-filled-syringe.
Preliminary Response of Patent Owner Regeneron Pharmaceuticals, Inc. filed Dec. 15, 2021, in Case PGR2021-00117 (U.S. Pat. No. 10,857,231) (92 pgs.) (later withdrawn by the PTAB).
Press Release, Novartis receives FDA approval of Xolair® (omalizumab self-injection with prefilled syringe across all indications for appropriate patients, (Apr. 12, 2021).
Press Release, Re generon Reports Fourth Quarter and Full Year 2022 Financial and Operating Results (Feb. 3, 2023).
RAPTIVA®, *Physician's Desk Reference*, 59th Ed., Thompson PDR (NJ), pp. 1350-1354 (2005).
*Rational Design of Stable Protein Formulations: Theory and Practice*, John F. Carpenter and Mark C. Manning (eds), Pharmaceutical Biotechnology, vol. 13, DOI 10.1007/978-1-4615-0557-0, © Springer Science+Business Media New York (2002).
REMICADE®, *Physician's Desk Reference*, 59th Ed., Thompson PDR (NJ), pp. 1117-1122 (2005).
Request for Ex Parte Reexamination of U.S. Pat. No. 10,464,992 (Furfine et al.), filed Feb. 11, 2020 (78 pgs.).
Resume of Reiner Gentz, Ph.D., as submitted to the USPTO on Jan. 7, 2021, in Inter Partes Review No. IPR2021-00402, 3 pgs.
Reply of Patentee in Opposition of EP 2944306 (Mar. 20, 2023).
SIMULECT®, *Physician's Desk Reference*, 59th Ed., Thompson PDR (NJ), pp. 325 & 2367-2369 (2005).
U.S. Food & Drug Administration, "Guidance for Industry—Container Closure Systems for Packaging Human Drugs and Biologics," (56 pgs.) (May 1999), submitted in IPR2023-00462 as Exhibit 1038.
U.S. Food & Drug Administration, "Guidance for Industry—Q6B Specification: Test Procedures and Acceptance Criteria for Biotechnological/Biological Products,"(24 pgs.) (Aug. 1999), submitted in IPR2023-00462 as Exhibit 1047.
U.S. Food & Drug Administration, "Points to Consider in the Manufacture and Testing of Monoclonal Antibody Products for Human Use,"pp. 1-50 (Feb. 28, 1997), submitted in IPR2023-00620 as Exhibit 1020.
USPTO Communication on Ex Parte Reexamination of US10464992 USPTO Communication, pp. 1-12, published Apr. 1, 2020.
Van Bruggen et al., "VEGF antagonism reduces edema formation and tissue damage after ischemia/reperfusion injury in the mouse brain,"*The Journal of Clinical Investigation*, 104(11): pp. 1613-1620 (1999).
Wang, "Lyophilization and Development of Solid Protein Pharmaceuticals,"*International Journal of Pharmaceutics*, 203: pp. 1-60 (2000).
Wurm, "Production of Recombinant Protein Therapeutics in Cultivated Mammalian Cells," *Nature Biotechnology*, 22(11): pp. 1393-1398 (Nov. 2004).
XOLAIR®, *Physician's Desk Reference*, 59th Ed., Thompson PDR (NJ), pp. 1359-1362 (2005).
Zaltrap® (ziv-aflibercept), FDA Marketing Information, Initial US Approval 2012, 17 pp.
Zhao et al., "Increasing the homogeneity, stability and activity of human serum albumin and interferon-α2b fusion protein by linker engineering,"*Protein Expression and Purification*, 61:73-77 (2008).

CITRATE BUFFERED VEGF ANTAGONIST FORMULATIONS

CROSS-REFERENCE TO RELATED APPLICATIONS

This application is a continuation of U.S. patent application Ser. No. 16/535,610 filed Aug. 8, 2019 and granted on Dec. 8, 2020 as U.S. Pat. No. 10,857,231, which is a continuation of U.S. patent application Ser. No. 15/692,893 filed Aug. 31, 2017 and granted on Sep. 10, 2019 as U.S. Pat. No. 10,406,226, which is a continuation of U.S. patent application Ser. No. 15/342,989, filed on Nov. 3, 2016, which is a continuation of U.S. patent application Ser. No. 15/064,343, filed on Mar. 8, 2016 and granted on Dec. 6, 2016 as U.S. Pat. No. 9,511,140, which is a continuation of U.S. patent application Ser. No. 14/550,385, filed on Nov. 21, 2014 and granted on Aug. 16, 2016 as U.S. Pat. No. 9,416,167, which is a continuation of U.S. patent application Ser. No. 13/909,745, filed on Jun. 4, 2013 and granted on Dec. 30, 2014 as U.S. Pat. No. 8,921,316, which is a continuation of U.S. patent application Ser. No. 13/428,510, filed on Mar. 23, 2012 and granted on Apr. 29, 2014 as U.S. Pat. No. 8,710,004, which is a continuation of U.S. patent application Ser. No. 13/343,214, filed on Jan. 4, 2012 and granted on Mar. 26, 2013 as U.S. Pat. No. 8,404,638, which is a division of U.S. patent application Ser. No. 12/835,065, filed on Jul. 13, 2010 and granted on Feb. 7, 2012 as U.S. Pat. No. 8,110,546, which is a continuation of U.S. patent application Ser. No. 11/387,256, filed on Mar. 22, 2006, which claims the benefit of priority under 35 USC § 119(e) of U.S. Provisional Application No. 60/665,125, filed on Mar. 25, 2005, all of which are herein specifically incorporated by reference in their entirety.

BACKGROUND OF THE INVENTION

Field of the Invention

The present invention is directed to pharmaceutical formulations comprising agents capable of inhibiting vascular endothelial growth factor (VEGF), and to methods for making and using such formulations. The invention includes pharmaceutical formulations having increased stability.

STATEMENT OF RELATED ART

Vascular endothelial growth factor (VEGF) expression is nearly ubiquitous in human cancer, consistent with its role as a key mediator of tumor neoangiogenesis. Blockade of VEGF function, by binding to the molecule or its VEGFR-2 receptor, inhibits growth of implanted tumor cells in multiple different xenograft models (see, for example, Gerber et al. (2000) Cancer Res. 60:6253-6258). A soluble VEGF-specific fusion protein antagonist, termed a "VEGF trap" has been described (Kim et al. (2002) Proc. Natl. Acad. Sci. USA 99:11399-404; Holash et al. (2002) Proc. Natl. Acad. Sci. USA 99:11393-8), which references are specifically incorporated by reference in their entirety.

Lyophilization (freeze drying under controlled conditions) is commonly used for long term storage of proteins. The lyophilized protein is substantially resistant to degradation, aggregation, oxidation, and other degenerative processes while in the freeze-dried state (see, for example, U.S. Pat. No. 6,436,897).

BRIEF SUMMARY OF THE INVENTION

Stable formulations of a VEGF-specific fusion protein antagonist are herein provided. The pharmaceutically acceptable formulations of the invention comprise the VEGF "trap" antagonist with a pharmaceutically acceptable carrier. In specific embodiments, liquid and freeze-dried, or lyophilized formulations are provided.

In a first aspect, the invention features a stable liquid formulation of a VEGF-specific fusion protein antagonist, comprising a fusion protein comprising a receptor component consisting essentially of an immunoglobulin-like (Ig) domain 2 of a first VEGF receptor and Ig domain 3 of a second VEGF receptor, and a multimerizing component, one or more buffers, and one or more thermal stabilizers. In a specific embodiment of the VEGF-specific fusion protein antagonist, the first VEGF receptor is Flt1 and the second VEGF receptor is Flk1 or Flt4. In a more specific embodiment the fusion protein has the amino acid sequence of SEQ ID NO:2 or SEQ ID NO:4. In one embodiment, the buffer is a phosphate buffer and/or citrate. More preferably, the buffers are phosphate and citrate. In one embodiment, the thermal stabilizers are NaCl and/or sucrose. More preferably, the thermal stabilizers are both NaCl and sucrose.

In a specific embodiment, the stable liquid formulation of a VEGF-specific fusion protein antagonist comprises 1-10 mM phosphate buffer, 1-10 mM citrate, 25-150 mM NaCl, 5-30% sucrose, 10-50 mg/ml of the fusion protein, at a pH of about 6-6.5. In a more specific embodiment, the stable liquid formulation comprises 5 mM phosphate buffer, 5 mM citrate buffer, 100 mM NaCl, 20% sucrose, 25 mg/ml of the fusion protein, at a pH of about 6.0. Additionally, polysorbate may be present, for example 0.05-0.15% polysorbate 20. The stable liquid formulation of the VEGF-specific fusion protein antagonist of the invention exhibits little or no precipitation after storage of a 25 mg/ml VEGF formulation for about 6 months at −80° C. and little or no precipitation after storage for 6 months at 5° C.

In a second aspect, the invention features a high concentration stable liquid formulation of a VEGF antagonist comprising 1-50 mM histidine, 25-150 mM NaCl, 5-30% sucrose, 50-100 mg/ml of the fusion protein, at a pH of about 6-6.5, and either 0.1-0.5% polysorbate or 1-5% PEG. In a more specific embodiment, the high concentration stable liquid formulation comprises 10 mM histidine, 50 mM NaCl, 5-20% sucrose, 50-100 mg/ml of the fusion protein, at a pH of about 6.0-6.5, with either 0.1% polysorbate (e.g., polysorbate 20) or 3% PEG (e.g., PEG 3350).

In a third aspect, the invention features a pre-lyophilized formulation of a vascular endothelial growth factor (VEGF)-specific fusion protein antagonist, comprising (i) a fusion protein comprising a receptor component consisting essentially of an immunoglobulin-like (Ig) domain 2 of a first VEGF receptor and Ig domain 3 of a second VEGF receptor, and a multimerizing component, (ii) a buffer, (iii) an organic co-solvent or bulking agent, and (iv) one or more lyoprotectants. In various embodiments, the buffer is histidine, the organic co-solvent or bulking agent is PEG, and the lyoprotectant(s) is at least one of glycine and sucrose. In one embodiment, the pre-lyophilized formulation of the invention does not contain a preservative.

In one embodiment of the pre-lyophilized formulation of the invention, the formulation comprises 5-50 mM histidine, 0.1-3.0% PEG, 0.25-3.0% glycine, 0.5-6.0% sucrose, and 5-75 mg/ml of the fusion protein, at a pH of about 6.0-6.5. In any embodiment, the pre-lyophilized formulation may further comprise up to 0.05 mM citrate and/or 0.003-0.05% polysorbate. The polysorbate present may be, for example, polysorbate 20.

In a more specific embodiment, the pre-lyophilized formulation comprises about 10 mM histidine, about 1.5% PEG 3350, about 0.75% glycine, about 2.5% sucrose, and about 12.5 to 75 mg/ml VEGF-specific fusion protein, at a pH of about 6.25. In specific embodiments, the fusion protein comprises the protein sequence of SEQ ID NO:4, present as a multimer, e.g., a dimer. In separate embodiments, the reconstituted formulation is 2 times the concentration of the pre-lyophilized formulation, e.g., a 20 mg fusion protein/ml pre-lyophilized formulation is reconstituted to a final formulation of 60 mg fusion protein/mi. Generally, the lyophilized formulation is reconstituted with sterile water suitable for injection. In one embodiment, the reconstitution liquid may be bacteriostatic water.

In a preferred embodiment, the pre-lyophilized formulation consists essentially of about 10 mM histidine, about 1.5% PEG 3350, about 0.75% glycine, about 2.5% sucrose, and about 50 mg/ml of the fusion protein having the sequence of SEQ ID NO:4 as a dimer, at a pH of about 6.25. Citrate (less than or equal to about 0.02 mM) and/or polysorbate (less than or equal to about 0.0005%) may be present. Optionally, the pre-lyophilized formulation does not contain a preservative, a phosphate buffer, and/or more than trace amounts of NaCl. In one embodiment, the pre-lyophilized formulation consists of about 10 mM histidine, about 1.5% PEG 3350, about 0.75% glycine, about 2.5% sucrose, and about 50 mg/ml of the VEGF trap protein (SEQ ID NO:4), pH 6.3, and upon reconstitution contains 20 mM histidine, 3% PEG, 1.5% glycine, about 5% sucrose, and about 100 mg/ml VEGF trap protein.

In a fourth aspect, the invention features a method of producing a lyophilized formulation of a VEGF-specific fusion protein antagonist, comprising subjecting the pre-lyophilized formulation of the invention to lyophilization to generate a lyophilized formulation. The lyophilized formulation may be lyophilized by any method known in the art for lyophilizing a liquid.

In a fifth related aspect, the invention features a method of producing a reconstituted lyophilized formulation of a VEGF-specific fusion protein antagonist, comprising reconstituting the lyophilized formulation of the invention to a reconstituted formulation. In one embodiment, the reconstituted formulation is twice the concentration of the pre-lyophilized formulation, e.g., the method of the invention comprises: (a) producing a pre-lyophilized formulation of a VEGF-specific fusion protein antagonist, (b) subjecting the pre-lyophilized formulation of step (a) to lyophilization; and (c) reconstituting the lyophilized formulation of step (b).

In specific embodiments of the method of producing a reconstituted lyophilized formulation, a pre-lyophilized solution is present in a vial as a 25 mg VEGF-specific fusion protein antagonist per ml solution of pre-lyophilized formulation, which is lyophilized and reconstituted to a 50 mg/ml solution. In another embodiment, a 30 mg/ml pre-lyophilized solution is lyophilized and reconstituted to a 60 mg/ml solution. In another embodiment, a 40 mg/ml pre-lyophilized solution is lyophilized and reconstituted to a 80 mg/ml solution. In another embodiment, a 12.5 mg/ml pre-lyophilized solution is lyophilized and reconstituted to a 25 mg/ml solution. In another embodiment, a 50 mg/ml pre-lyophilized solution is lyophilized and reconstituted to a 100 mg/ml solution. In another embodiment, a 75 mg/ml pre-lyophilized solution is lyophilized and reconstituted to a 150 mg/ml solution. Preferably, the reconstituted lyophilized formulation does not contain a preservative.

Other objects and advantages will become apparent from a review of the ensuing detailed description.

DETAILED DESCRIPTION OF THE INVENTION

The present invention is not limited to particular methods, and experimental conditions described, as such methods and conditions may vary. It is also to be understood that the terminology used herein is for the purpose of describing particular embodiments only, and is not intended to be limiting unless indicated, since the scope of the present invention will be limited only by the appended claims.

As used in this specification and the appended claims, the singular forms "a", "an", and "the" include plural references unless the context clearly dictates otherwise. Thus for example, references to "a method" include one or more methods, and/or steps of the type described herein and/or which will become apparent to those persons skilled in the art upon reading this disclosure.

Unless stated otherwise, all technical and scientific terms and phrases used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned herein are incorporated herein by reference.

General Description

Safe handling and administration of formulations comprising proteins represent significant challenges to pharmaceutical formulators. Proteins possess unique chemical and physical properties that present stability problems: a variety of degradation pathways exist for proteins, implicating both chemical and physical instability. Chemical instability includes deamination, aggregation, clipping of the peptide backbone, and oxidation of methionine residues. Physical instability encompasses many phenomena, including, for example, aggregation.

Chemical and physical stability can be promoted by removing water from the protein. Lyophilization (freeze-drying under controlled conditions) is commonly used for long-term storage of proteins. The lyophilized protein is substantially resistant to degradation, aggregation, oxidation, and other degenerative processes while in the freeze-dried state. The lyophilized protein is normally reconstituted with water optionally containing a bacteriostatic preservative (e.g., benzyl alcohol) prior to administration.

Definitions

The term "carrier" includes a diluent, adjuvant, excipient, or vehicle with which a composition is administered. Carriers can include sterile liquids, such as, for example, water and oils, including oils of petroleum, animal, vegetable or synthetic origin, such as, for example, peanut oil, soybean oil, mineral oil, sesame oil and the like.

The term "excipient" includes a non-therapeutic agent added to a pharmaceutical composition to provide a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The term "lyophilized" or "freeze-dried" includes a state of a substance that has been subjected to a drying procedure such as lyophilization, where at least 50% of moisture has been removed.

The phrase "bulking agent" includes a compound that is pharmaceutically acceptable and that adds bulk to a lyo cake. Generally, acceptable bulking agents known to the art include, for example, carbohydrates, including simple sugars such as dextrose, ribose, fructose and the like, alcohol sugars such as mannitol, inositol and sorbitol, disaccharides including trehalose, sucrose and lactose, naturally occurring polymers such as starch, dextrans, chitosan, hyaluronate, proteins (e.g., gelatin and serum albumin), glycogen, and synthetic monomers and polymers. In the formulations of the invention, PEG 3350 is an organic co-solvent which is used to stabilize the fusion protein when agitated, mixed, or handled, and as a bulking agent to help produce an acceptable bulk.

The term "lyoprotectant" includes a substance that may be added to a freeze-dried or lyophilized formulation to help maintain protein structure when freeze-dried or lyophilized.

A "preservative" includes a bacteriostatic, bacteriocidal, fungistatic or fungicidal compound that is generally added to formulations to retard or eliminate growth of bacteria or other contaminating microorganisms in the formulations. Preservatives include, for example, benzyl alcohol, phenol, benzalkonium chloride, m-cresol, thimerosol, chlorobutanol, methylparaben, propylparaben and the like. Other examples of pharmaceutically acceptable preservatives can be found in the USP.

VEGF Antagonists

A VEGF antagonist is a compound capable of blocking or inhibiting the biological action of vascular endothelial growth factor (VEGF), and includes fusion proteins capable of trapping VEGF. In a preferred embodiment, the VEGF antagonist is the fusion protein of SEQ ID NO:2 or 4; more preferably, SEQ ID NO.4. In specific embodiments, the VEGF antagonist is expressed in a mammalian cell line such as a CHO cell and may be modified posttranslationally. In a specific embodiment, the fusion protein comprises amino acids 27-457 of SEQ ID NO.4 and is glycosylated at Asn residues 62, 94, 149, 222 and 308.

The VEGF antagonist of the methods and formulations of the invention can be prepared by any suitable method known in the art, or that comes to be known. The VEGF antagonist is preferably substantially free of protein contaminants at the time it is used to prepare the pharmaceutically acceptable formulation. By "substantially free of protein contaminants" is meant, preferably, that at least 90% of the weight of protein of the VEGF-specific fusion protein antagonist preparation used for making a formulation is VEGF fusion protein antagonist protein, more preferably at least 95%, most preferably at least 99%. The fusion protein is preferably substantially free of aggregates. "Substantially free of aggregates" means that at least 90% of the weight of fusion protein is not present in an aggregate at the time the fusion protein is used to prepare the pharmaceutically effective formulation. The fusion protein of the methods and formulations of the invention may contain low or trace amounts of compounds as a result of the purification process, for example, low or trace amounts of citrate and/or polysorbate. In one embodiment of the pre-lyophilized formulation of the invention containing about 50 mg of fusion protein/ml, citrate may be present at a concentration of about 0.02 mM and/or polysorbate may be present at a concentration of about 0.0005%. If the pre-lyophilized formulation is reconstituted after lyophilization to half of the original volume (e.g., 100 mg/ml of fusion protein), the resulting concentrations may be 0.04 mM citrate and/or 0.001% polysorbate.

Lyophilization and Lyophilized Formulations

In one aspect of the invention, a pharmaceutically acceptable formulation comprising a VEGF-specific fusion protein antagonist is provided, wherein the formulation is a freeze-dried or lyophilized formulation. Lyophilized formulations can be reconstituted into solutions, suspensions, emulsions, or any other suitable form for administration or use. Lyophilized formulations are typically first prepared as liquids, then frozen and lyophilized. The total liquid volume before lyophilization can be less, equal to, or more than, the final reconstituted volume of the lyophilized formulation. The lyophilization process is well known to those of ordinary skill in the art, and typically includes sublimation of water from a frozen formulation under controlled conditions.

Lyophilized formulations can be stored at a wide range of temperatures. Lyophilized formulations may be stored below 25° C., for example, refrigerated at 4° C., or at room temperature (e.g., approximately 25° C.). Preferably, lyophilized formulations are stored below about 25° C., more preferably, at about 4-20° C.; below about 4° C.; below about −20° C.; about −40° C.; about −70° C., or about −80° C.

Lyophilized formulations are typically reconstituted for use by addition of an aqueous solution to dissolve the lyophilized formulation. A wide variety of aqueous solutions can be used to reconstitute a lyophilized formulation. Preferably, lyophilized formulations are reconstituted using water. Lyophilized formulations are preferably reconstituted with a solution consisting essentially of water (e.g., USP WFI, or water for injection) or bacteriostatic water (e.g., USP WFI with 0.9% benzyl alcohol). However, solutions comprising buffers and/or excipients and/or one or more pharmaceutically acceptable carriers can also be used.

Freeze-dried or lyophilized formulations are typically prepared from liquids, that is, from solutions, suspensions, emulsions, and the like. Thus, the liquid that is to undergo freeze-drying or lyophilization preferably comprises all components desired in a final reconstituted liquid formulation. As a result, when reconstituted, the freeze-dried or lyophilized formulation will render a desired liquid formulation upon reconstitution. A preferred liquid formulation used to generate a freeze-dried or lyophilized formulation comprises a VEGF-specific fusion protein antagonist in a pharmaceutically effective amount, a buffer, a stabilizer, and a bulking agent. Freeze-dried or lyophilized formulations preferably comprise histidine, since histidine, in comparison to phosphate, is more effective at stabilizing the fusion protein when the fusion protein is lyophilized. Organic co-solvents, such as PEG 3350, are used to stabilize the fusion protein when agitated, mixed, or handled. A lyoprotectant is preferably used in freeze-dried or lyophilized formulations. Lyoprotectants help to maintain the secondary structure of proteins when freeze-dried or lyophilized. Two preferred example lyoprotectants are glycine and sucrose, which are preferably used together.

Stable Liquid Formulations

In one aspect, the invention provides a stable pharmaceutically acceptable formulation comprising a VEGF-specific fusion protein antagonist, wherein the formulation is a liquid formulation. Preferably, the liquid formulation comprises a pharmaceutically effective amount of the fusion protein. The formulation can also comprise one or more pharmaceutically acceptable carriers, buffers, bulking agents, stabilizers, preservatives, and/or excipients. An example of a pharmaceutically acceptable liquid formulation comprises a VEGF-specific fusion protein antagonist in a pharmaceutically effective amount, a buffer, a co-solvent, and one or more stabilizers.

A preferred liquid formulation comprises phosphate buffer, an organic co-solvent, and one or more thermal stabilizers to minimize formation of aggregates and low molecular weight products when stored, and about 10 mg/ml to about 50 mg/ml fusion protein, wherein the formulation is from about pH 6.0-6.5. A preferred liquid formulation comprises about 5 mM phosphate buffer, about 5 mM citrate, about 100 mM NaCl, about 25% sucrose, and about 1050 mg/ml fusion protein, wherein the formulation is at a pH of about 6.0; optionally polysorbate may be present (e.g., 0.1% polysorbate 20). Although either NaCl or sucrose can be used as a stabilizer, a combination of NaCl and sucrose has been established to stabilize the fusion protein more effectively than either individual stabilizer alone.

Stability is determined in a number of ways at specified time points, including determination of pH, visual inspection of color and appearance, determination of total protein content by methods known in the art, e.g., UV spectroscopy, SDS-PAGE, size-exclusion HPLC, bioassay determination of activity, isoelectric focusing, and isoaspartate quantification. In one example of a bioassay useful for determining VEGF antagonist activity, a BAF/3 VEGFR1/EPOR cell line is used to determine VEGF165 binding by the VEGF-specific fusion protein antagonist of the invention.

Formulations, whether liquid or freeze-dried and lyophilized, can be stored in an oxygen-deprived environment. Oxygen-deprived environments can be generated by storing the formulations under an inert gas such as, for example, argon, nitrogen, or helium.

EXAMPLES

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only to the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

Example 1. Stability of a 50 mg/ml Liquid Formulation of VEGF Trap

A liquid formulation containing 10 mM phosphate, 50 mM NaCl, 0.1% polysorbate 20, 20% sucrose, and 50 mg/ml VEGF trap (SEQ ID NO.4), pH 6.25, was stored at 5° C. and samples tested at 3, 6, 9, 12, 18 and 24 months. Stability was determined by SE-HPLC. The results, shown in Table 1, show that 98.6% and 98.3% of VEGF trap protein remained intact (non-degraded) at 12 and 24 months, respectively. Turbidity was measured at $OD_{405}$ nm; and percent recovered protein by size exclusion HPLC.

TABLE 1

Stability of 50 mg/ml VEGF Trap Protein When Stored at 5° C. (VGFT-SS065)

| Months | Visual Appearance | Turbidity | pH | % VEGF Trap Recovered | % VEGF Trap Native Configuration |
|---|---|---|---|---|---|
| 0 | Pass | 0.00 | 6.2 | 100 | 99.0 |
| 3 | Pass | 0.00 | 6.2 | 102 | 98.8 |
| 6 | Pass | 0.01 | 6.2 | 103 | 98.7 |
| 9 | Pass | 0.01 | 6.3 | 102 | 98.2 |
| 12 | Pass | 0.01 | 6.3 | 106 | 98.6 |
| 18 | Pass | 0.00 | 6.3 | 103 | 98.4 |
| 24 | Pass | 0.00 | 6.2 | 93 | 98.3 |

A liquid formulation containing 10 mM phosphate, 50 mM NaCl, 3% PEG 3350, 20% sucrose, and 50 mg/ml VEGF trap (SEQ ID NO.4), pH 6.25, was stored at 5° C. and samples tested at 3, 6, 9, 12, 18 and 24 months. Stability results are shown in Table 2.

TABLE 2

Stability of 50 mg/ml VEGF Trap Protein When Stored at 5° C. (VGFT-SS065)

| Months | Visual Appearance | Turbidity | pH | % VEGF Trap Recovered | % VEGF Trap Native Configuration |
|---|---|---|---|---|---|
| 0 | Pass | 0.00 | 6.2 | 100 | 99.0 |
| 3 | Pass | 0.00 | 6.2 | 100 | 98.8 |
| 6 | Pass | 0.01 | 6.3 | 103 | 98.5 |
| 9 | Pass | 0.00 | 6.3 | 103 | 98.3 |
| 12 | Pass | 0.01 | 6.3 | 110 | 98.3 |
| 18 | Pass | 0.00 | 6.3 | 113 | 98.0 |
| 24 | Pass | 0.01 | 6.2 | 90 | 97.8 |

Example 2. Stability of a 75 mg/ml Liquid Formulation of VEGF Trap

A liquid formulation containing 10 mM phosphate, 50 mM NaCl, 0.1% polysorbate 20, 20% sucrose, and 75 mg/ml VEGF trap (SEQ ID NO.4), pH 6.25, was stored at 5° C. and samples tested at 0, 1, 2.3, 3, 9, 12 and 15 months. Stability results are shown in Table 3.

TABLE 3

Stability of 75 mg/ml VEGF Trap Protein When Stored at 5° C. (VGFT-SS101)

| Months | Visual Appearance | Turbidity | pH | % VEGF Trap Recovered | % VEGF Trap Native Configuration |
|---|---|---|---|---|---|
| 0 | Pass | 0.00 | 6.2 | 100 | 97.1 |
| 1 | Pass | 0.00 | 6.2 | 96 | 97.0 |
| 2.3 | Pass | 0.00 | 6.2 | 98 | 96.7 |
| 3 | Pass | 0.00 | 6.2 | 97 | 96.1 |
| 9 | Pass | −0.01 | 6.0 | 101 | 96.0 |
| 12 | Pass | 0.00 | 6.3 | 110 | 94.5 |
| 15 | Pass | 0.00 | 6.3 | 92 | 95.6 |

A liquid formulation containing 10 mM phosphate, 50 mM NaCl, 300 PEG 3350, 2000 sucrose, and 75 mg/ml VEGF trap (SEQ ID NO:4), pH 6.25, was stored at 5° C. and samples tested at 0, 1, 2.3, 3, 9, 12 and 15 months. Stability results are shown in Table 4.

TABLE 4

Stability of 75 mg/ml VEGF Trap Protein When Stored at 5° C. (VGFT-SS101)

| Months | Visual Appearance | Turbidity | pH | % VEGF Trap Recovered | % VEGF Trap Native Configuration |
|---|---|---|---|---|---|
| 0 | Pass | 0.00 | 6.2 | 100 | 96.8 |
| 1 | Pass | 0.00 | 6.2 | 99 | 96.7 |
| 2.3 | Pass | 0.00 | 6.2 | 97 | 96.3 |
| 3 | Pass | 0.00 | 6.2 | 89 | 95.6 |
| 9 | Pass | −0.01 | 6.2 | 98 | 95.4 |
| 12 | Pass | −0.01 | 6.3 | 112 | 94.1 |
| 15 | Pass | 0.00 | 6.3 | 98 | 94.8 |

Example 3. Stability of a 100 mg/ml Liquid Formulation of VEGF Trap

A liquid formulation containing 10 mM phosphate, 50 mM NaCl, 0.10% polysorbate 20, 20% sucrose, and 100 mg/ml VEGF trap (SEQ ID NO:4), pH 6.25, was stored at 5° C. and samples tested at 0, 1, 2.3, 3, 9, 12 and 15 months. Stability results are shown in Table 5.

TABLE 5

Stability of 100 mg/ml VEGF Trap Protein Stored at 5° C. (VGFT-SS101)

| Months | Visual Appearance | Turbidity | pH | % VEGF Trap Recovered | % VEGF Trap Native Configuration |
|---|---|---|---|---|---|
| 0 | Pass | 0.00 | 6.3 | 100 | 96.7 |
| 1 | Pass | 0.00 | 6.2 | 92 | 96.6 |
| 2.3 | Pass | 0.00 | 6.2 | 92 | 96.2 |
| 6 | Pass | 0.00 | 6.2 | 99 | 95.5 |
| 9 | Pass | −0.01 | 6.2 | 92 | 95.5 |
| 12 | Pass | −0.01 | 6.2 | 110 | 93.9 |
| 15 | Pass | 0.00 | 6.3 | 108 | 94.8 |

A liquid formulation containing 10 mM phosphate, 50 mM NaCl, 3% PEG 3350, 20% sucrose, and 100 mg/ml VEGF trap (SEQ ID NO.4), pH 6.25, was stored at 5° C. and samples tested at 0, 1, 2.3, 3, 9, 12 and 15 months. Stability results are shown in Table 6.

TABLE 6

Stability of 100 mg/ml VEGF Trap Protein Stored at 5° C. (VGFT-SS101)

| Months | Visual Appearance | Turbidity | pH | % VEGF Trap Recovered | % VEGF Trap Native Configuration |
|---|---|---|---|---|---|
| 0 | Pass | 0.00 | 6.3 | 100 | 96.5 |
| 1 | Pass | 0.01 | 6.2 | 94 | 96.2 |
| 2.3 | Pass | 0.01 | 6.2 | 93 | 95.7 |
| 6 | Pass | 0.01 | 6.2 | 102 | 94.6 |
| 9 | Pass | 0.00 | 6.2 | 95 | 94.6 |
| 12 | Pass | 0.00 | 6.3 | 96 | 92.8 |
| 15 | Pass | 0.01 | 6.3 | 102 | 93.9 |

Example 4. Further Embodiments of Stable VEGF Trap Formulations

In one embodiment, the invention provides a stable liquid VEGF-binding fusion protein (VEGF trap) formulation comprising 5 mM phosphate, 5 mM citrate, 100 mM NaCl, 0.1% Polysorbate 20, 20% sucrose, 25 mg/ml VEGF trap protein, pH 6.0. This formulation can either be delivered subcutaneously or diluted and delivered by intravenous infusion. Due to the high osmolality of this formulation, it is diluted 3-fold to achieve an iso-osmolar solution for intravenous administration. Stability studies showed less than about 1% degradation was detected after 3 years of storage at 2-8° C.

In one embodiment, the invention features a lyophilized formulation which is preferably concentrated two-fold from the pre-lyophilized formulation to the post-lyophilized formulation, e.g., 50 to 100 mg/ml; 75 to 150 mg/ml, or 100 to 200 mg/ml VEGF trap protein. In one specific embodiment, the pre-lyophilized formulation comprises 10 mM histidine, 1.5% PEG 3350, 0.75% glycine, 2.5% sucrose, 50 mg/ml VEGF trap protein, pH 6.3, and is reconstituted to a formulation comprising 20 mM histidine, 3% PEG 3350, 1.5% glycine, 5% sucrose, 100 mg/ml VEGF trap protein, pH 6.3.

Example 5. Stability and Activity of Lyophilized and Liquid

The stability of a reconstituted lyophilized formulation was determined over a 6 month period. The pre-lyophilized formulation contained 10 mM histidine, 1.5% PEG 3350, 2.5% sucrose, 0.75% glycine and 50 mg/ml VEGF trap protein. After lyophilization, the reconstituted formulation contained 20 mM histidine, 3% PEG 3350, 5% sucrose, 1.5% glycine, and 100 mg/ml VEGF trap protein (SEQ ID NO:4). The results are shown in Table 7. Activity was determined in a cell based bioassay which directly measures the ability of the VEGF trap to inhibit the biological effects of human VEGF on a mouse Baf/3 VEGFR1/EpoR cell line. Therefore, this bioassay directly measures the biological activity of the protein. The results are expressed as percent relative potency (test sample $IC_{50}$/reference VEGF $IC_{50}$ standard×100). The binding affinity of VEGF to the VEGF trap is measured using a sensitive ELISA that specifically measures free VEGF in equilibrated mixtures containing VEGF and various concentrations of the VEGF trap. Results are expressed as percent relative binding ($IC_{50}$ of test sample/ICH, of reference×100). Measured pH ranged between 6.3-6.5. All solutions where visually clear. The concentration of VEGF trap recovered was determined with a UV spectrophotometer as mg/ml at A280 nm. The percent VEGF trap recovered in the native configuration (main peak purity) was determined with SE-HPLC.

TABLE 7

Stability of VEGF Trap Lyophilized Formulation Stored at 5° C. (VGT-RS475)

| Months | Bioassay | Binding Assay | % Recovered | % Native Configuration |
|---|---|---|---|---|
| 0 | 120 | 126 | 97.9 | 98.7 |
| 1 | 117 | 74 | 97.9 | 98.6 |
| 1 + 24 hr | 126 | 72 | 99.0 | 98.5 |
| 1 + 4 hr | 94 | 81 | 101.5 | 98.2 |
| 3 | 101 | 98 | 98.1 | 98.6 |
| 3 + 24 hr | 65 | 94 | 98.1 | 98.2 |

TABLE 7-continued

Stability of VEGF Trap Lyophilized
Formulation Stored at 5° C. (VGT-RS475)

| Months | Bioassay | Binding Assay | % Recovered | % Native Configuration |
|---|---|---|---|---|
| 6 + 4 hr | | | 96.9 | 98.7 |
| 6 + 24 hr | | | 98.8 | 98.6 |

A formulation containing about 5 mM phosphate, 5 mM citrate, 100 mM NaCl, 0.1% polysorbate 20, 20% sucrose, and 25 mg/ml VEGF trap protein was tested for stability and activity over 36 months when stored at 5° C. The results are shown in Table 8. All samples were clear and colorless as determined by visual inspection. pH ranged from 6.0-6.1. *Binding assay results for two measurements (1 and 2 months) are expressed directly and not as a percent of the standard.

TABLE 8

Stability and Activity of Liquid
Formulation (VGT-FS405)

| Months | % Native Configuration | Bio-assay | Binding Assay | Protein Content mg/ml |
|---|---|---|---|---|
| 0 | 99.7 | 106 | 72 | 25.0 |
| 1 | 99.9 | 119 | 4.4 pM* | 25.2 |
| 2 | 99.6 | 102 | 5.4 pM* | 25.1 |
| 3 | 99.6 | 97 | 88 | 25.1 |
| 6 | 99.6 | 101 | 106 | 25.0 |
| 9 | 99.4 | 89 | 126 | 25.4 |
| 12 | 99.5 | 85 | 95 | 25.2 |
| 18 | 99.4 | 99 | 81 | 25.5 |
| 24 | 99.3 | 75 | 95 | 25.6 |
| 36 | 98.8 | 109 | 79 | 25.6 |

We claim:

1. A formulation comprising:
   10-50 mg/ml of a vascular endothelial growth factor (VEGF) antagonist fusion protein comprising amino acids 27-457 of SEQ ID NO:4,
   a buffer comprising citrate,
   an organic co-solvent comprising polysorbate, and
   a stabilizing agent comprising a sugar, an amino acid or both,
   wherein said VEGF antagonist fusion protein exhibits less than about 3% degradation after 15 months of storage at 5° C.

2. The formulation of claim 1, wherein the fusion protein comprises amino acids 27-457 of SEQ ID NO:4 and is glycosylated at Asn residues 62, 94, 149, 222 and 308.

3. The formulation of claim 1, wherein the buffer comprises 1-10 mM citrate.

4. The formulation of claim 1, wherein the buffer comprises about 5 mM citrate.

5. The formulation of claim 1, wherein the buffer further comprises phosphate.

6. The formulation of claim 3, wherein said stabilizing agent comprises both a sugar and an amino acid.

7. The formulation of claim 6, wherein said sugar is sucrose.

8. The formulation of claim 7, wherein said sugar comprises 5-30% sucrose.

9. The formulation of claim 7, wherein said sugar comprises 5-20% sucrose.

10. The formulation of claim 9, wherein the organic co-solvent is polysorbate 20.

11. The formulation of claim 1, wherein said stabilizing agent comprises an amino acid.

12. The formulation of claim 7, wherein said formulation further comprises a tonicity agent.

13. The formulation of claim 9, wherein said organic co-solvent is 0.05%-0.15% polysorbate 20.

14. The formulation of claim 13, wherein said formulation comprises 10 mg/mL VEGF antagonist fusion protein.

15. A vial comprising the formulation of claim 6.

16. A vial comprising the formulation of claim 7.

17. A vial comprising the formulation of claim 9.

18. A vial comprising the formulation of claim 10.

19. A vial comprising the formulation of claim 11.

20. A vial comprising the formulation of claim 13.

21. A pre-filled syringe comprising the formulation of claim 6.

22. A pre-filled syringe comprising the formulation of claim 7.

23. A pre-filled syringe comprising the formulation of claim 9.

24. A pre-filled syringe comprising the formulation of claim 10.

25. A pre-filled syringe comprising the formulation of claim 13.

26. A vial comprising the formulation of claim 14.

27. A pre-filled syringe comprising the formulation of claim 14.

28. A pre-filled syringe comprising the formulation of claim 14.

* * * * *

SEQUENCE LISTING

<160> NUMBER OF SEQ ID NOS: 4

<210> SEQ ID NO 1
<211> LENGTH: 1453
<212> TYPE: DNA
<213> ORGANISM: Artificial sequence
<220> FEATURE:
<223> OTHER INFORMATION: Synthetic

<400> SEQUENCE: 1

```
aagcttgggc tgcaggtcga tcgactctag aggatcgatc cccgggcgag ctcgaattcg      60
caaccaccat ggtcagctac tgggacaccg gggtcctgct gtgcgcgctg ctcagctgtc     120
tgcttctcac aggatctagt tccggaggta gaccctttcgt agagatgtac agtgaaatcc    180
ccgaaattat acacatgact gaaggaaggg agctcgtcat tccctgccgg gttacgtcac    240
ctaacatcac tgttacttta aaaagtttc cacttgacac tttgatccct gatggaaaac     300
gcataatctg ggacagtaga aagggcttca tcatatcaaa tgcaacgtac aaagaaatag    360
ggcttctgac ctgtgaagca acagtcaatg gcatttgta taagacaaac tatctcacac    420
atcgacaaac caatacaatc atagatgtgg ttctgagtcc gtctcatgga attgaactat    480
ctgttggaga aaagcttgtc ttaaattgta cagcaagaac tgaactaaat gtggggattg    540
acttcaactg ggaatacccct tcttcgaagc atcagcataa gaaacttgta aaccgagacc    600
taaaaaccca gtctgggagt gagatgaaga aattttttgag caccttaact atagatggtg    660
taacccggag tgaccaagga ttgtacacct gtgcagcatc cagtgggctg atgaccaaga    720
agaacagcac atttgtcagg gtccatgaaa agggcccggg cgacaaaact cacacatgcc    780
caccgtgccc agcacctgaa ctcctggggg gaccgtcagt cttcctcttc cccccaaaac    840
ccaaggacac cctcatgatc tcccggaccc ctgaggtcac atgcgtggtg gtggacgtga    900
gccacgaaga ccctgaggtc aagttcaact ggtacgtgga cggcgtggag gtgcataatg    960
ccaagacaaa gccgcgggag gagcagtaca acagcacgta ccgtgtggtc agcgtcctca   1020
ccgtcctgca ccaggactgg ctgaatggca aggagtacaa gtgcaaggtc tccaacaaag   1080
ccctcccagc ccccatcgag aaaaccatct ccaaagccaa agggcagccc cgagaaccac   1140
aggtgtacac cctgccccca tcccgggatg agctgaccaa gaaccaggtc agcctgacct   1200
gcctggtcaa aggcttctat cccagcgaca tcgccgtgga gtgggagagc aatgggcagc   1260
cggagaacaa ctacaagacc acgcctcccg tgctggactc cgacggctcc ttcttcctct   1320
```

-continued

```
atagcaagct caccgtggac aagagcaggt ggcagcaggg gaacgtcttc tcatgctccg   1380
tgatgcatga ggctctgcac aaccactaca cgcagaagag cctctccctg tctccgggta   1440
aatgagcggc cgc                                                      1453
```

<210> SEQ ID NO 2
<211> LENGTH: 458
<212> TYPE: PRT
<213> ORGANISM: Artificial sequence
<220> FEATURE:
<223> OTHER INFORMATION: synthetic

<400> SEQUENCE: 2

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Gly Arg Pro Phe Val Glu
            20                  25                  30

Met Tyr Ser Glu Ile Pro Glu Ile Ile His Met Thr Glu Gly Arg Glu
        35                  40                  45

Leu Val Ile Pro Cys Arg Val Thr Ser Pro Asn Ile Thr Val Thr Leu
    50                  55                  60

Lys Lys Phe Pro Leu Asp Thr Leu Ile Pro Asp Gly Lys Arg Ile Ile
65                  70                  75                  80

Trp Asp Ser Arg Lys Gly Phe Ile Ile Ser Asn Ala Thr Tyr Lys Glu
                85                  90                  95

Ile Gly Leu Leu Thr Cys Glu Ala Thr Val Asn Gly His Leu Tyr Lys
            100                 105                 110

Thr Asn Tyr Leu Thr His Arg Gln Thr Asn Thr Ile Ile Asp Val Val
        115                 120                 125

Leu Ser Pro Ser His Gly Ile Glu Leu Ser Val Gly Glu Lys Leu Val
    130                 135                 140

Leu Asn Cys Thr Ala Arg Thr Glu Leu Asn Val Gly Ile Asp Phe Asn
145                 150                 155                 160

Trp Glu Tyr Pro Ser Ser Lys His Gln His Lys Lys Leu Val Asn Arg
                165                 170                 175

Asp Leu Lys Thr Gln Ser Gly Ser Glu Met Lys Lys Phe Leu Ser Thr
            180                 185                 190

Leu Thr Ile Asp Gly Val Thr Arg Ser Asp Gln Gly Leu Tyr Thr Cys
        195                 200                 205

Ala Ala Ser Ser Gly Leu Met Thr Lys Lys Asn Ser Thr Phe Val Arg
    210                 215                 220

Val His Glu Lys Gly Pro Gly Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335
```

```
Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415

Leu Tyr Ser Lys Leu Thr Val Asp Lys Ser Arg Trp Gln Gln Gly Asn
        420                 425                 430

Val Phe Ser Cys Ser Val Met His Glu Ala Leu His Asn His Tyr Thr
435                 440                 445

Gln Lys Ser Leu Ser Leu Ser Pro Gly Lys
    450                 455

<210> SEQ ID NO 3
<211> LENGTH: 1377
<212> TYPE: DNA
<213> ORGANISM: Artificial sequence
<220> FEATURE:
<223> OTHER INFORMATION: synthetic

<400> SEQUENCE: 3
atggtcagct actgggacac cggggtcctg ctgtgcgcgc tgctcagctg tctgcttctc      60
acaggatcta gttccggaag tgataccggt agaccttccg tagagatgta cagtgaaatc     120
cccgaaatta tacacatgac tgaaggaagg gagctcgtca ttccctgccg ggttacgtca     180
cctaacatca ctgttacttt aaaaaagttt ccacttgaca ctttgatccc tgatggaaaa     240
cgcataatct gggacagtag aaagggcttc atcatatcaa tgcaacgta caaagaaata     300 gggcttctga cctgtgaagc aacagtcaat gggcatttgt ataagacaaa ctatctcaca     360
catcgacaaa ccaatacaat catagatgtg gttctgagtc cgtctcatgg aattgaacta     420
tctgttggag aaaagcttgt cttaaattgt acagcaagaa ctgaactaaa tgtggggatt     480
gacttcaact gggaataccc ttcttcgaag catcagcata gaaacttgt aaaccgagac     540 ctaaaaaccc agtctgggag tgagatgaag aaattttga gcaccttaac tatagatggt     600
gtaacccgga gtgaccaagg attgtacacc tgtgcagcat ccagtgggct gatgaccaag     660
aagaacagca catttgtcag ggtccatgaa aaggacaaaa ctcacacatg cccaccgtgc     720
ccagcacctg aactcctggg gggaccgtca gtcttcctct tccccccaaa acccaaggac     780
accctcatga tctcccggac ccctgaggtc acatgcgtgg tggtggacgt gagccacgaa     840
gaccctgagg tcaagttcaa ctggtacgtg gacggcgtgg aggtgcataa tgccaagaca     900
aagccgcggg aggagcagta acagcacg taccgtgtgg tcagcgtcct caccgtcctg     960
caccaggact ggctgaatgg caaggagtac aagtgcaagg tctccaacaa agccctccca    1020
gcccccatcg agaaaaccat ctccaaagcc aaagggcagc cccgagaacc acaggtgtac    1080
accctgcccc catcccggga tgagctgacc aagaaccagg tcagcctgac ctgcctggtc    1140
aaaggcttct atcccagcga catcgccgtg gagtgggaga gcaatgggca gccggagaac    1200
aactacaaga ccacgcctcc cgtgctggac tccgacggct ccttcttcct ctacagcaag    1260
ctcaccgtgg acaagagcag gtggcagcag gggaacgtct tctcatgctc cgtgatgcat    1320
```
gaggctctgc acaaccacta cacgcagaag agcctctccc tgtctccggg taaatga    1377

<210> SEQ ID NO 4
<211> LENGTH: 458
<212> TYPE: PRT
<213> ORGANISM: Artificial sequence
<220> FEATURE:
<223> OTHER INFORMATION: synthetic

<400> SEQUENCE: 4

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
                20                  25                  30

Phe Val Glu Met Tyr Ser Glu Ile Pro Glu Ile Ile His Met Thr Glu
            35                  40                  45

Gly Arg Glu Leu Val Ile Pro Cys Arg Val Thr Ser Pro Asn Ile Thr
        50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu

```
                355                 360                 365
Leu Thr Lys Asn Gln Val Ser Leu Thr Cys Leu Val Lys Gly Phe Tyr
        370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
            435                 440                 445

Gln Lys Ser Leu Ser Leu Ser Pro Gly Lys
        450                 455
```